United States Patent
Marcus

(10) Patent No.: US 10,485,593 B2
(45) Date of Patent: *Nov. 26, 2019

(54) INTERMAXILLARY FIXATION DEVICE AND METHOD OF USING SAME

(71) Applicant: Jeffrey R. Marcus, Chapel Hill, NC (US)

(72) Inventor: Jeffrey R. Marcus, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/980,551

(22) Filed: Dec. 28, 2015

(65) Prior Publication Data

US 2016/0106486 A1    Apr. 21, 2016

Related U.S. Application Data

(63) Continuation of application No. 14/618,111, filed on Feb. 10, 2015, now Pat. No. 9,220,552, which is a continuation of application No. 13/399,282, filed on Feb. 17, 2012, now Pat. No. 8,979,529, which is a continuation of application No. 12/329,263, filed on Dec. 5, 2008, now Pat. No. 8,118,850.

(Continued)

(51) Int. Cl.
| | |
|---|---|
| *A61C 8/00* | (2006.01) |
| *A61B 17/86* | (2006.01) |
| *A61C 5/00* | (2017.01) |
| *A61C 7/00* | (2006.01) |
| *A61F 5/058* | (2006.01) |
| *A61C 7/36* | (2006.01) |
| *A61B 17/60* | (2006.01) |

(52) U.S. Cl.
CPC .......... *A61B 17/8605* (2013.01); *A61B 17/60* (2013.01); *A61C 5/007* (2013.01); *A61C 7/00* (2013.01); *A61C 7/36* (2013.01); *A61C 8/0096* (2013.01); *A61F 5/05891* (2013.01)

(58) Field of Classification Search
CPC .. A61C 5/007; A61C 7/00; A61C 7/36; A61C 8/00; A61C 8/0096; A61B 17/663; A61B 17/80; A61B 17/8061; A61B 17/8071; A61B 17/8085
See application file for complete search history.

(56) References Cited

U.S. PATENT DOCUMENTS

| | | | |
|---|---|---|---|
| 49,779 A | 9/1865 | Montignani | |
| 83,195 A | 10/1868 | Middleton | |

(Continued)

FOREIGN PATENT DOCUMENTS

| | | |
|---|---|---|
| DE | 29615779 | 1/1997 |
| DE | 19826860 A1 | 4/1999 |

(Continued)

OTHER PUBLICATIONS

Non-Final Office Action on U.S. Appl. No. 12/329,306 dated Dec. 1, 2016.

(Continued)

*Primary Examiner* — Si Ming Ku
(74) *Attorney, Agent, or Firm* — Lerner, David, Littenberg, Krumholz & Mentlik, LLP

(57) ABSTRACT

A medical apparatus including a bar with a first attachment loop, a second attachment and a plurality of hooks, wherein the medical apparatus is an arch bar.

15 Claims, 7 Drawing Sheets

Related U.S. Application Data

(60) Provisional application No. 61/012,557, filed on Dec. 10, 2007, provisional application No. 61/012,561, filed on Dec. 10, 2007.

(56) References Cited

U.S. PATENT DOCUMENTS

| | | | |
|---|---|---|---|
| 592,250 | A | 10/1897 | Kuenzle |
| 1,638,006 | A | 8/1927 | Aderer |
| 2,481,177 | A * | 9/1949 | Tofflemire ............... A61C 7/00 433/18 |
| 2,502,902 | A * | 4/1950 | Tofflemire .......... A61F 5/05891 433/23 |
| 2,580,821 | A | 1/1952 | Nicola |
| 3,474,779 | A | 10/1969 | Wall, Jr. |
| 4,202,328 | A | 5/1980 | Sukkarie |
| 4,230,104 | A | 10/1980 | Richter |
| 4,639,219 | A | 1/1987 | Gagin |
| 4,797,095 | A | 1/1989 | Armstrong et al. |
| 4,904,188 | A * | 2/1990 | Baurmash ................ A61C 5/00 433/215 |
| 5,087,202 | A | 2/1992 | Krenkel |
| 5,137,158 | A | 8/1992 | Brockway |
| 5,839,899 | A | 11/1998 | Robinson |
| 5,842,856 | A | 12/1998 | Casey |
| 5,853,092 | A | 12/1998 | Goodman et al. |
| 6,053,919 | A | 4/2000 | Talos et al. |
| 6,086,365 | A | 7/2000 | Fields |
| 6,227,861 | B1 | 5/2001 | Cartledge et al. |
| 6,257,884 | B1 | 7/2001 | Chang |
| 6,595,774 | B1 | 7/2003 | Risse |
| 6,730,091 | B1 | 5/2004 | Pfefferle et al. |
| 6,827,574 | B2 | 12/2004 | Payton |
| 6,896,514 | B2 | 5/2005 | Devincenzo |
| 7,322,987 | B2 | 1/2008 | Schendel |
| 7,351,058 | B2 | 4/2008 | Fore et al. |
| 8,118,850 | B2 | 2/2012 | Marcus |
| 8,282,635 | B1 | 10/2012 | Amato |
| 8,662,889 | B2 | 3/2014 | Baker |
| 8,979,529 | B2 | 3/2015 | Marcus |
| 2001/0018176 | A1 | 8/2001 | Branemark |
| 2002/0013586 | A1 | 1/2002 | Justis et al. |
| 2002/0143336 | A1 | 10/2002 | Hearn |
| 2002/0150856 | A1 * | 10/2002 | Payton ................... A61C 7/00 433/8 |
| 2003/0160552 | A1 | 8/2003 | Bacho et al. |
| 2004/0086824 | A1 | 5/2004 | Kesling |
| 2004/0152046 | A1 | 8/2004 | Minoretti et al. |
| 2005/0059971 | A1 | 3/2005 | Michelson |
| 2005/0090825 | A1 | 4/2005 | Pfefferle et al. |
| 2005/0261690 | A1 | 11/2005 | Binder et al. |
| 2005/0282115 | A1 | 12/2005 | Gedebou |
| 2006/0069389 | A1 | 3/2006 | Knopfle |
| 2006/0078849 | A1 | 4/2006 | Parks |
| 2007/0190475 | A1 | 8/2007 | Fore et al. |
| 2007/0254259 | A1 | 11/2007 | Devincenzo et al. |
| 2007/0259306 | A1 | 11/2007 | Raines et al. |
| 2008/0050691 | A1 * | 2/2008 | Baughman ............... A61C 7/00 433/18 |
| 2009/0036889 | A1 | 2/2009 | Callender |
| 2011/0152946 | A1 | 6/2011 | Frigg et al. |
| 2011/0152951 | A1 | 6/2011 | Baker |

FOREIGN PATENT DOCUMENTS

| | | |
|---|---|---|
| DE | 19859503 | 7/2000 |
| DE | 20007908 U1 | 12/2000 |
| DE | 19859506 B4 | 7/2005 |
| EP | 1 468 656 | 10/2004 |
| EP | 1 385 435 B1 | 12/2006 |
| FR | 2760631 | 9/1998 |
| GB | 1 231 425 | 11/1967 |
| JP | 11-164843 | 6/1999 |
| WO | WO-97/27815 | 8/1997 |
| WO | WO-99/15115 | 4/1999 |
| WO | WO-2007/095577 | 8/2007 |
| WO | WO-2010/025263 | 3/2010 |
| WO | WO-2011/063368 | 5/2011 |

OTHER PUBLICATIONS

Non-Final Office Action on U.S. Appl. No. 12/329,306 dated May 23, 2016.
Communication issued on EP Application 08868823.9, dated Nov. 3, 2014.
Extended European Search Report issued on European Application 08859747.1, dated Mar. 16, 2015.
Final Office Action issued in U.S. Appl. No. 12/329,306 and dated Oct. 19, 2011.
Final Office Action on U.S. Appl. No. 13/399,282, dated May 14, 2013.
Final Office Action received for U.S. Appl. No. 12/329,263 dated Feb. 2, 2011.
Final Office Action received for U.S. Appl. No. 12/329,306 dated Feb. 28, 2011 (10 pgs.).
International Search Report and Written Opinion for PCT/US2008/085680 dated Jan. 29, 2009.
International Search Report and Written Opinion for PCT/US2008/085685 dated Feb. 6, 2009.
IPRP received in PCT/US2008/085685 dated Jun. 24, 2010.
Non-final Office Action for U.S. Appl. No. 12/329,306 dated Nov. 9, 2010.
Non-Final Office Action on U.S. Appl. No. 12/329,306, dated Oct. 27, 2015.
Non-Final Office Action on U.S. Appl. No. 13/399,282, dated Dec. 3, 2012.
Non-Final Office Action on U.S. Appl, 13/399,282, dated Aug. 6, 2014.
Non-Final Office Action on U.S. Appl. No. 14/618,111, dated Jun. 23, 2015.
Non-final Office Action received for U.S. Appl. No. 12/329,263 dated Sep. 20, 2010.
Non-final Office Action received for U.S. Appl. No. 12/329,263 dated May 31, 2011.
Non-Final Office Action; in re U.S. Appl. No. 12/329,306; dated Jul. 6, 2011; Applicant: Jeffrey R. Marcus; (11 pgs.).
Notice of Allowance issued in U.S. Appl. No. 12/329,263 and dated Oct. 21, 2011.
Notice of Allowance on U.S. Appl. No. 13/399,282, dated Dec. 29, 2014.
Notice of Allowance on U.S. Appl. No. 14/618,111 dated Aug. 31, 2015.
Supplementary European Search Report for Application No. EP 08868823, dated Jul. 22, 2013, 5 pages.
Communication issued on European Application 08859747.1, dated Mar. 11, 2016.
Extended European Search Report and Written Opinion for EP17001891 dated Apr. 5, 2018.

* cited by examiner

INTERMAXILLARY FIXATION DEVICE AND METHOD OF USING SAME

CROSS-REFERENCE TO RELATED APPLICATIONS

This application is a continuation of U.S. patent application Ser. No. 14/618,111, filed Feb. 10, 2015, which is a continuation of U.S. patent application Ser. No. 13/399,282, filed Feb. 17, 2012, now U.S. Pat. No. 8,979,529, which is a continuation of U.S. patent application Ser. No. 12/329,263, filed on Dec. 5, 2008, now U.S. Pat. No. 8,118,850, which in turn claims the benefit of U.S. Provisional Patent Application Nos. 61/012,557, filed Dec. 10, 2007, and 61/012,561, filed Dec. 10, 2007, the entire contents of which are incorporated herein by reference for any and all purposes.

FIELD

The invention is generally related to maxillofacial/dental devices. More specifically, the invention is related to devices for the maxillary and/or mandibular fixation or stabilization.

BACKGROUND

The fixation or stabilization of the upper and lower dental occlusal arches to one another is known as intermaxillary fixation (IMF), also known as maxillo-mandibular fixation (MMF). IMF has historically been a necessity in the treatment of all reconstructive jaw procedures.

The earliest methods for providing IMF consisted of wiring techniques, in which metallic wires were placed around one or more (adjacent) teeth at their base(s) and were then twisted down to the teeth in a secure manner. When a wire is passed around a tooth (or teeth) at the base in such a way, it may be termed a circumdental wire ligature (CW). Multiple CW's can be placed along the span of the dental arch in a series, or the wire may also be fashioned such that a single continuous strand incorporates multiple teeth along the arch securely. In whatever manner this is accomplished, both upper and lower arches are so treated, and subsequently the jaws are then secured to one another with wire loops or elastics incorporating single or multiple CW or the opposing jaws, thus accomplishing IMF.

Arch bars (or arch wires) are known to those of skill in the art. Arch bars involve the use of a linear metal bar or wire that may be applied and secured to the dental arch form. Arch bars typically have a plurality of hooks/tabs facing in a single direction. The arch bars and their corresponding hooks are placed in opposing directions for the upper and lower jaws so that wire loops or elastics could securely affix the jaws together. Multiple types of arch bar have been proposed. Arch bars have the advantage of stability. The relatively rigid bar spanning along the dental arch provides stability along the upper border of either jaw even when a fracture is present between teeth. A plurality of hooks allows placement of elastics or wire loops between the jaws at varying angles to potentially affect varying, advantageous tension vectors. The two common methods of securing all arch bars to date are (1) via circumdental wire ligatures, placed around the teeth in routine fashion but incorporating the arch bar; and (2) via orthodontic adhesives of a variety of types.

However, both methods suffer drawbacks. For example, the most common means to secure arch bars is via multiple circumdental wire ligatures. This is a time-consuming process, associated with significant discomfort and potential for dental injury. The wire ligatures themselves are uncomfortable and often must be adjusted/tightened by the treating physician. Removal of arch bars applied using CW's, is equally uncomfortable; there is further associated potential for dental injury; in some, removal requires operative anesthesia.

While orthodontic adhesives are known, they too have disadvantages, in large part due to the conditions under which IMF is performed. For example, IMF is often performed by a surgical specialist, who is unfamiliar with the techniques and procedures used by orthodontists and dentists in the area of dental adhesives. The procedures are also, many times, conducted in a trauma setting where damage and blood loss limit the ability to work with such adhesives—which require a relatively clean, dry field for efficacy.

Adhesive techniques and circumdental wiring techniques both require adequate dentition. Both techniques may be severely limited or even precluded in conditions for dental injury, loss, or preexisting poor dental health.

Another method of IMF is also known by utilizing individual screws, placed in the bone between tooth roots, with a portion of the screw projecting external to the gingival or mucosa. Two or more IMF screws are typically placed into each of the upper and lower jaws. A wire loop is then either wrapped around the exposed portion of two opposing screws, or through a hole that is drilled through each of the two opposing screw heads, to provide IMF.

The advantages of IMF screw fixation are speed of placement and comfort. The screws rarely require adjustment, are well-tolerated, and are easily removed. However, IMF screws do not provide stability along the dental arch as does an arch bar. Ideally, IMF is used not only for immobilization, but also for accurate restoration of occlusion. For fractures occurring between teeth, IMF screws do not provide upper border stabilization nor flexible technical application methods to optimize occlusion. Finally, it is difficult (if not impossible) to apply elastics between IMF screws. Elastic IMF is safer than wiring the jaws together, and is often preferred for specific fracture types in which the surgeon would prefer the patient to have guided mobility of the jaws rather than relative immobilization.

Most of the technologies proposed for IMF technologies to date have been developed by orthodontists and oral surgeons. These dental specialists have been understandably inclined to consider only methods which involve fixation to teeth, a concept that has been historically accepted and perpetuated since the early 1900's. The most significant developments in reconstructive jaw surgery in the modern era have focused largely on methods for internal fixation (plating), rather than IMF. However, internal fixation is not a replacement for IMF, nor does is preclude the need for IMF in most cases, which is still a mandatory procedure for reconstruction of the dental arches.

Despite early developments in dental arch fixation technology, and advanced developments in other dental areas, there is currently no way to anchor existing arch bars to bone using existing technologies.

SUMMARY OF THE INVENTION

In one aspect, a medical apparatus is provided comprising a bar comprising a first attachment loop, a second attachment loop, and a plurality of hooks, wherein the bar is an arch bar and the first attachment loop and the second attachment loop are located distally to one another. In some embodiments, the bar further comprises one or more additional attachment loops located between the first and second attachment loops. In other embodiments, the bar further comprises a third attachment loop located about midway between the first and the second attachment loop. In yet other embodiments, the attachment loops are capable of receiving a screw to attach the arch bar to a mandible, a maxilla, and/or a prosthedontic device. In yet other embodiments, the medical apparatus of claim 1, wherein the first attachment loop and/or the second attachment loop is a compound attachment loop.

In some embodiments, the first attachment loop is attached to the arch bar via a first stem and the second attachment loop is attached to the arch bar via a second stem. In some such embodiments, the first and the second stems are bendable.

In some embodiments, the hooks are capable of receiving a wire, an elastic, and/or other flexible, rigid, or semi-rigid materials.

In some embodiments, the bar is a bendable bar. In some embodiments, the length of the arch bar may vary according to user defined needs.

In another aspect, a medical apparatus is provided comprising a first and second arch bar, as described above and herein, wherein the first arch bar is attached to a subject's maxilla, the second arch bar is attached to a subject's mandible, and the first arch bar is attached to the second arch bar via a wire, an elastic, and/or other flexible, rigid, or semi-rigid materials.

In another aspect, a method is provided comprising stabilizing a mandibular arch or a maxillary arch using the arch bars described above and herein. In some embodiments, the method further comprises bending the arch bar to approximate the mandibular arch or the maxillary arch, inserting a first screw through the first attachment loop, inserting a second screw through the second attachment loop, and screwing the first and the second screws into a mandible or a maxilla.

In another aspect, a method is provided comprising fixating a mandibular arch and a maxillary arch using a first and second arch bar, as described above and herein, wherein the first arch bar is attached to a subject's maxilla, the second arch bar is attached to a subject's mandible, and the first arch bar is attached to the second arch bar via a wire, an elastic, and/or other flexible, rigid, or semi-rigid materials. Such methods may include bending the first arch bar to approximate the maxillary arch; bending the second arch bar to approximate the mandibulary arch; inserting screws through the attachment loops of the first and second arch bars; screwing the screws through the attachment loops of the first arch bar into the maxilla; and screwing the screws through the attachment loops of the second arch bar into the mandible. Such methods may also include applying a fastener such as a wire, an elastic, or other flexible, or semi-rigid material between the hooks of the first arch bar and the hooks of the second arch bar to enact intermaxillary fixation, and/or establish dental occlusion.

The methods described herein may be used to restore or create dental occlusion between existing native dentition, dental implants, or other dental appliances. In other embodiments the methods are used to treat fracture, restore dental occlusion, fixate dental occlusion, and/or reconstruct maxillary and/or mandibular abnormalities.

In one aspect, a medical apparatus is provided comprising a bar comprising a first attachment loop assembly, a second attachment loop assembly, and a plurality of hooks, wherein the medical apparatus is a dynamic arch bar and the first attachment loop assembly and the second attachment loop assembly are movably engaged to the bar. In some embodiments, the bar further comprises one or more additional attachment loop assemblies located between the first and second attachment loop assemblies. In other embodiments, the bar further comprises a third attachment loop assembly. In yet other embodiments, the attachment loop assemblies each comprise a bracket, an attachment loop, a stem, and a set screw. In some such embodiments, the attachment loops are capable of receiving a screw to attach the arch bar to a mandible, a maxilla, and/or a prosthedontic device.

In some embodiments, the hooks are capable of receiving a wire or an elastic material, or other flexible, rigid, or semi-rigid material. In other embodiments, the bar is a bendable bar.

In another aspect, a medical apparatus is provided comprising a first dynamic arch bar and a second dynamic arch bar, wherein the first dynamic arch bar is configured to be attached to a subject's maxilla, the second arch bar is configured to be attached to a subject's mandible, and the first arch bar is attached to the second arch bar via a wire, an elastic, or other flexible, rigid, or semi-rigid material.

In another aspect, a method is provided comprising using a first dynamic arch bar to fixate a maxillary arch of a subject and/or using a second dynamic arch bar to fixate a mandibular arch of a subject. In one embodiment, the method restores or creates dental occlusion between existing native dentition, dental implants, or other dental appliances. In another embodiment, the method further comprises bending the first dynamic arch bar to approximate the maxillary arch; bending the second dynamic arch bar to approximate the mandibulary arch; positioning the first and second attachment loop assemblies of the first and second dynamic arch bars on the bars, securing the first dynamic arch bar to the maxillary, a prosthedontic device, or a bone graft, securing the second dynamic arch bar to the mandible, a prosthedontic device, or a bond graft, and securing the first and second attachment loop assemblies of the first and second dynamic arch bars in place on the bars.

In some embodiments, the method further comprises applying a fastener between the hooks of the first dynamic arch bar and the hooks of the second dynamic arch bar to enact intermaxillary fixation, and/or establish dental occlusion. In some such embodiments, the fastener is a wire, an elastic, or other flexible, or semi-rigid material.

In yet another aspect, a method is provided comprising using a dynamic arch bar to stabilize a mandibular arch or a maxillary arch of a subject. In some embodiments, the method comprises bending the arch bar to approximate the mandibular arch or the maxillary arch, positioning the first and second attachment loop assemblies on the bar, securing the first and second attachment loop assemblies in place on the bar, and securing the arch bar to a mandible, a maxilla, a prosthedontic device, or a bone graft. In other embodiments, the method further comprises positioning a third attachment loop assembly on the bar, and securing the third attachment loop assembly in place on the bar. In some such embodiments, the attachment loop assemblies each comprise a set screw and the securing of the first and second attachment loop assemblies comprises setting the set screw. In other such embodiments, the arch bar assemblies comprise an attachment loop, and the securing the arch bar comprises inserting screws through the attachment loops and screwing the screws into the mandible, the maxilla, the prosthedontic device, or the bone graft.

In yet another aspect, a method of using a dynamic arch bar to reduce a fracture of the mandible or maxilla in a patient is provided, the method comprising bending the arch bar to approximate the mandibular arch or the maxillary arch, positioning the first and second attachment loop assemblies on the bar on either side of the fracture, securing the attachment loop assemblies to the bone on either side of the fracture via screws, reducing the fracture by pulling the screws toward one another, securing the first and second attachment loop assemblies in place on the bar.

DETAILED DESCRIPTION

Arch bars are described for providing stabilization and/or fixation between the mandible and maxilla using device(s) affixed to bone (native or graft) or prosthedontic appliances for use in applications including, but not limited to, treatment of fracture, restoration and fixation of dental occlusion, and maxillary and/or mandibular reconstruction with or without bone grafts. The arch bars may be affixed to bone, thus precluding the need for CW, or the use of adhesives.

Figure 1:
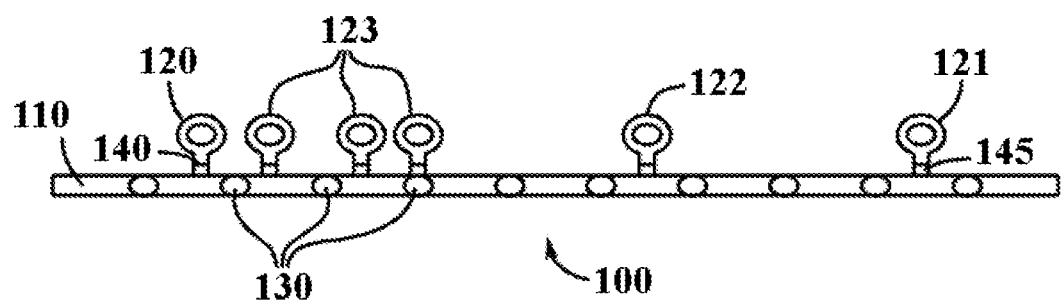
FIG. 1 is a frontal view of an arch bar prior to bending to approximate the shape of a mandible or a maxilla, according to one embodiment.
Figure 2:
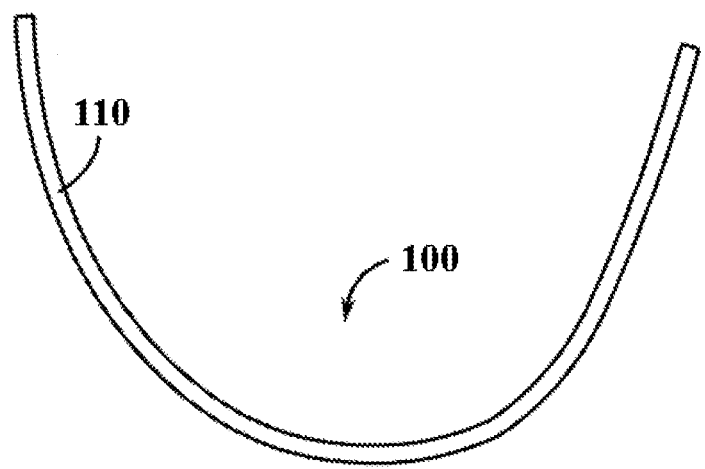
FIG. 2 is a top view of an arch bar bent into a shape to approximate a maxillary or mandibular arch, according to one embodiment.

As shown in FIG. 1, and according to one embodiment, an arch bar 100 is a bar 110 having a first attachment loop 120, a second attachment loop 121, and a plurality of hooks 130. The first attachment loop 120 is distally located to the second attachment loop 121 such that each end of the bar, may be secured to a bone such a mandible or maxilla, or a prosthedontic apparatus via the first and second attachment loops 120, 121. The attachment loops 120, 121 may be attached to the bar 110 via a stem 140, 145 that is rigid or bendable. The bar 110 may be bendable to approximate a maxillary or mandibular arch, for example as shown in FIG. 2.

As used herein, the term "bendable" is to mean that the item to which the term refers may be moved, or shaped, in response to the application of an external force. Further, once moved or bent, the item does not return to its previous position, without being acted upon by a second external force. In other words, the item is bent and stays bent, until bent into another shape or position.

As used herein, the term "rigid" is used to refer to an item that resists bending to a moderate force, but may be bent under extreme force as compared to a bendable item.

The bar may be made from a variety of materials known to those of skill in the art. For example the bar may be made from stainless steel, titanium, or other metals; acrylics; and/or polymers.

In some embodiments, the bar 110 has one or more additional attachment loops 122, 123 located between the first 120 and second 121 attachment loops. For example, the bar 110 may have a third attachment loop 122 located approximately midway between the first 120 and second 121 attachment loops, thereby providing an additional point of attachment for the bar.

The attachment loops 120, 121, 122, 123 provide a point at which the bar 110 may be secured to a maxilla, a mandible, or a prosthetic appliance using a screw, a bone screw, or other fastener known to those of skill in the art. In some embodiment, the one or more additional attachment loops refers to a third, a fourth, a fifth, a sixth, a seventh, or more attachment loops that are even spaced along a length of the bar 110, or at other predetermined positions.

The attachment loops 120, 121, 122, 123 may be integrally formed with the bar 110 as if a single piece of material were used and each portion cut or formed from the single piece. In other embodiments, the attachment loops 120, 121, 122, 123 are made from a separate piece of material and attached to the bar 110 via welding, adhesive, rivets, screws, or via other attachments known to those of skill in the art. The material from which the attachment loops 120, 121, 122, 123 may be made may be the same as the bar 110, or of a different material.

A variety of fasteners may be used to attach the bar 110 to a maxilla or a mandible. For example, such fasteners may include screws, rivets, bolts, staples, or other fastener known to those of skill in the art. The fasteners are attached to the maxilla or mandible via a variety of systems. For example, a hole for attaching the fastener may be pre-drilled in the maxilla or mandible, or the fastener may be a self-drilling or self-tapping fastener. The size of the fastener may also be varied depending upon the placement desired. For example, mandibles are typically thicker than maxillas and therefore a mandible is capable of receiving a longer and/or wider fastener than the maxilla. Fasteners may also be flush mounted to the gingiva or may have a relief from the gingival surface so that there is some amount of externalization for a surgeon or dental professional to easily find the fastener when removal of the device is desired.

Figure 3:
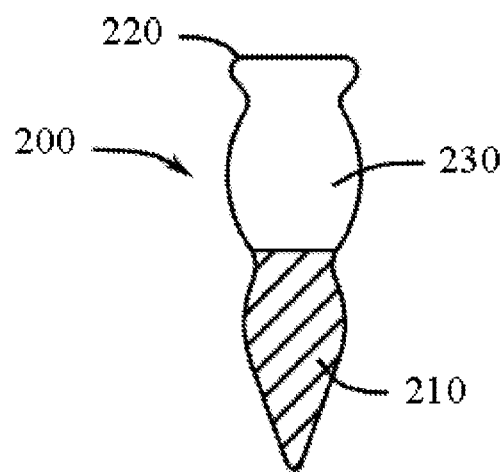
FIG. 3 is a side view of a screw, according to one embodiment.

As a non-limiting example of such fasteners, screws 200 may used to attach the bar 110 to a maxilla or mandible. For example, FIG. 3 shows a side view of a screw 200, according to one embodiment. The screw 200 has a head 210 and an inclined plane portion 220. The screw 200 may have threading that extends to the head 210 to allow for full insertion of the screw 200 in to the bone. The screw 200 may alternatively, have a post 230 that would project from the gingiva, or mucosa, when screwed into a mandible or maxilla. Such a post 230 would allow the surgeon or other dental professional to readily locate the screw for removal. The drive mechanism for the screw 200 may be of any type known to those of skill in the art. For example the screw 200 may have a slot drive, a Phillips drive, star drive, an Allen drive, or a hex head. The screws may be designed to require tapping, they may be self-tapping, they may be self-drilling/self tapping, or other design known to those of skill in the art.

In some embodiments, the base of the head of the screw is of a larger diameter than a shaft of the screw to permit solid coaptation (via surface area contact) of the arch bar flange to the bone, much like a washer. Wire or elastics may then be placed between the arch bar opposing hooks 130, 330, or tabs, therefore a passage hole through the screw is not required, as was common with IMF screw fixation. The screw may project through the gingiva or mucosa for ease in removal, or it may be designed to sit flush with the bone. The screw design may be standard (tapping), self-tapping, self-drilling/tapping, or other desired style.

Insertion of screws 200 into a root should be avoided. In fact, it is desired that the screws 200 are inserted into the bone at a position between the roots of adjacent teeth. Therefore, the attachment loops 120, 121, 122, 123 may be appended from the arch bar 100 via a stem 140, 145 that is bendable. A bendable stem provides for the individual adjustment of each attachment loop to a position that allows for insertion of a screw into bone and between the roots of adjacent teeth, or for other adjustment of the position as desired by the surgeon or other medical professional.

Figure 4:
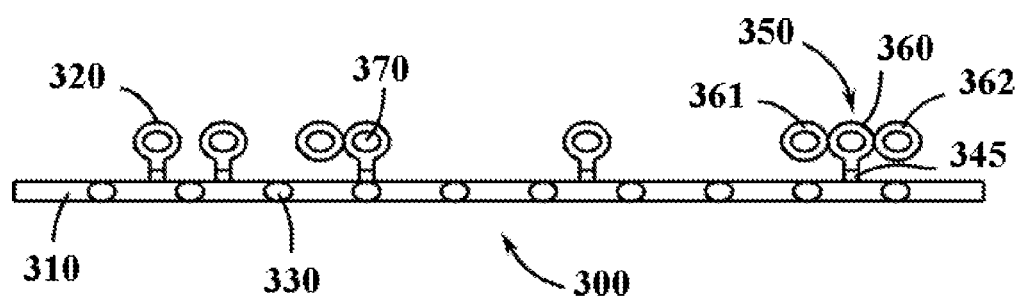
FIG. 4 is a frontal view of an arch bar with compound attachment loops, prior to bending to approximate the shape of a mandible or a maxilla, according to one embodiment.

Attachment loop positions may further be adjusted by providing compound attachment loops 350 in which at least two loops 360, 361 are provided per compound loop 350 as shown in FIG. 4. In such embodiments, any of the loops that corresponds to a position between the roots of adjacent teeth may be used to secure an arch bar 300 with a screw to the maxilla or mandible. Where the loop that is used is one of the side loops 361, 362 or the middle loop 360, the other side loop, or both side loops (if the middle loop is used) may be removed by cutting or breaking it free from the compound loop 350 to form a modified compound loop 370.

Figure 5:
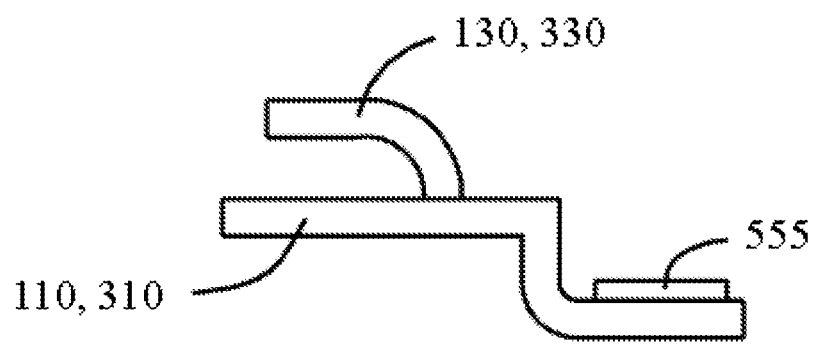
FIG. 5 is a side view of a hook, with cross-section of the bar, according to one embodiment.

As noted above, a plurality of hooks 130, 330 are attached to the bar 110, 310. As used herein, plurality may mean one, but typically means more than one, such as two, three, four, five, six, seven, eight, nine, ten, eleven, twelve, thirteen, fourteen, fifteen, sixteen, seventeen, eighteen, nineteen, or twenty. The hooks 130, 330 are used to attach a wire, an elastic such as a rubber band, or other device known to those of skill in the art, to the bar 110, 310 to immobilize, stabilize, or fixate the maxilla to the mandible, thus allowing for healing of the respective bones. A detailed side view of the hooks is shown in FIG. 5. In FIG. 5, the reference numeral 555 is used to identify an attachment loop that is characteristic of any of the above attachment loops or compound attachment loops.

As depicted in FIG. 5, the hooks 130, 330 may have the open part of the hook in a position opposed to the attachment loop. However, in other embodiments, the hook may have the open part of the hook turned toward the attachment loop. In such other embodiments, the attachment loops and hooks may be staggered in position so that the hook does not interfere with screw placement into attachment loop. The size, shape, and configuration of the hooks may vary according to design preferences. The common mandatory design element is the ability to satisfactorily allow placement of wire, elastic, or other fasteners.

Figure 6:
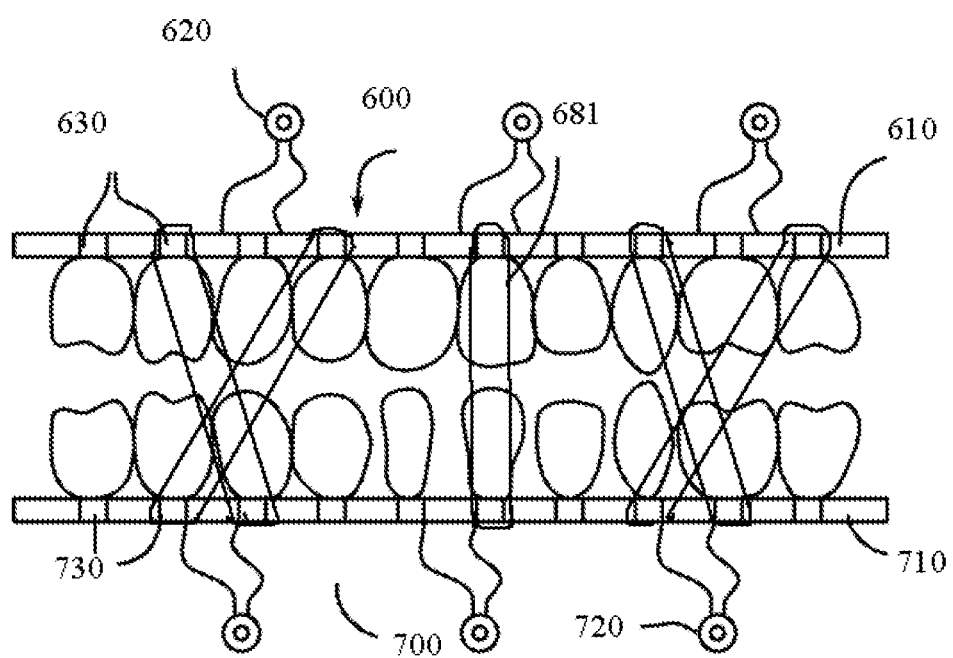
FIG. 6 is a panorex view of a full dental arch having a first and a second arch bar in place across the dentition, according to one embodiment.

In some aspects, the medical apparatus has two arch bars, as shown in FIG. 6. A first arch bar 600 is attached to the maxilla and a second arch bar 700 is attached to a mandible. The bars 610, 710 are attached in the same manner as above, i.e. with screws through the two or more attachment loops 620, 720. The hooks 620, 720 on each of the arch bars 600, 700 opposed to one another so that the securing wires 680, 681, 682, elastics such as rubber bands, or other attachment devices can be hooked to the arch bars 600, 700 on the maxilla and mandible. The securing wires 680, 681, 682 or other attachment devices may be separate entities as shown in FIG. 6, or a single wire may be intricately woven to attach arch bar 600 to arch bar 700, thus fixating the maxilla and/or mandible.

In another aspect, methods are provided for stabilizing a mandibular arch or a maxillary arch using the medical apparatuses described above. For example, the arch bar may be bent to approximate the mandibular arch or the maxillary arch of a patient in need of stabilization or fixation of the mandibular and/or maxillary arch. Screws are then inserted through the attachment loops, and the screws are then secured in the mandible and/or maxilla. If the attachment loop is not in line with a position that is between the roots of adjacent teeth, the attachment loop may be bent to such a position, or if a compound attachment loop is used, the appropriate loop is selected for use in attaching the arch bar to the maxilla or mandible.

In other embodiments, where both a mandibular and a maxillary arch bar are used, the methods also include securing a wire, an elastic, or other flexible or semi-rigid material between the hooks of the mandibular arch bar and the hooks of the maxillary arch bar. This may be done to establish intermaxillary fixation or dental occlusion. Such an arrangement is shown in FIG. 6. Such methods are known as wiring the jaws shut or intermaxillary fixation.

In another aspect, dynamic arch bars are described for providing stabilization and/or fixation between the mandible and maxilla using device(s) affixed to bone (native or graft) or prosthedontic appliances for use in applications including, but not limited to, treatment of fracture, restoration and fixation of dental occlusion, and maxillary and/or mandibular reconstruction with or without bone grafts. The arch bars may be affixed to bone, thus precluding the need for CW, or the use of adhesives. In addition, dynamic arch bars which include movable components, in particular movable attachment loop assemblies, provide additional features for surgeons or other professionals to adapt the arch bars to be used in a broader spectrum of applications.

Figure 7:
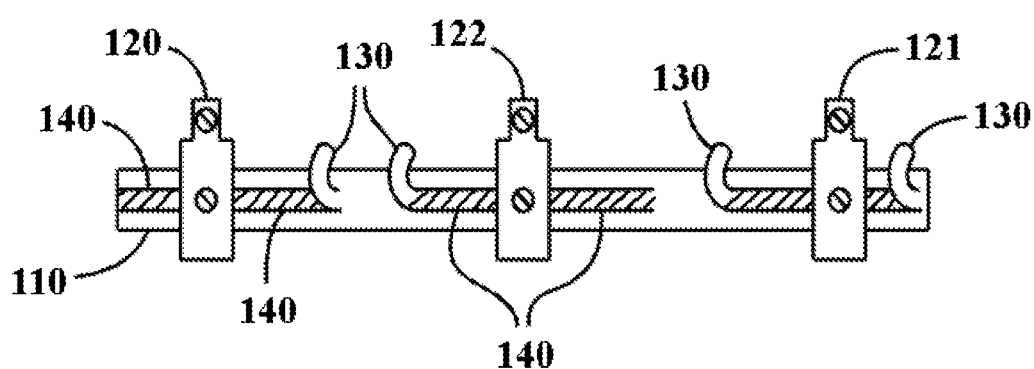
FIG. 7 is a frontal view of a dynamic arch bar according to one embodiment of the invention.

As shown in FIG. 7, and according to one embodiment, an arch bar 800 is a bar 810 having a first attachment loop assembly 820, a second attachment loop assembly 821, and a plurality of hooks 830. The first attachment loop assembly 820 is distally located to the second attachment loop assembly 821 such that each end of the bar 810, may be secured to a bone such a mandible or maxilla, or a prosthedontic apparatus via the first and second attachment loop assemblies 820, 821. In some cases, the bar 810 has a third attachment loop assembly 822, or even further attachment loop assemblies. The number of attachment loop assemblies may vary depending upon the patient to receive such an appliance, or the application in which the appliance is to be used. The arch bar 800 is dynamic in that the attachment loop assemblies 820, 821 are movably (i.e. dynamically) attached to the arch bar 800.

Arch bars such the dynamic arch bar, like those embodied above, may be bendable such that the arch bars may approximate a maxillary or mandibular arch. For example, FIG. 2 shows an arch bar that has been formed to approximate a maxillary or mandibular arch. As with all arch bars, the dynamic arch bar may be formed into a shape that approximates a maxillary or mandibular arch upon manufacture and minor adjustments may or may not be made by the surgeon or other medical profession that places the arch bar into use in a patient.

The bar, attachment loop assemblies, hooks, and screws may be made from a variety of materials known to those of skill in the art. For example the bar may be made from stainless steel, titanium, or other metals; acrylics; and/or polymers.

Figure 8A:
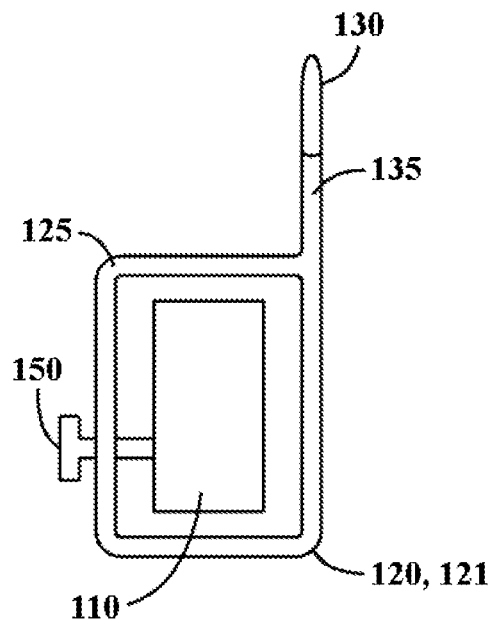
FIGS. 8A and 8B are side views of dynamic arch bar loop assembly brackets, according to two embodiments of the invention.
Figure 8B:
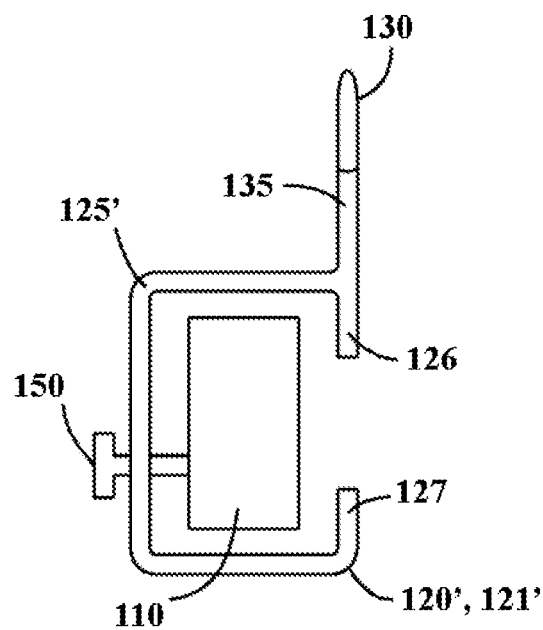

As shown in FIGS. 8A and 8B, an attachment loop assemblies 820, 821, 822 include a bracket 825, an attachment loop 830, and a set screw 850. The attachment loop assemblies 820, 821, 822 are attached to the bar 810 by a bracket 825 that may encircle (FIG. 8A) the bar 810. Alternatively, FIG. 8B, an attachment loop assembly 820', 821', may partially encircle the bar 810. In such alternative assemblies, the partially encircling bracket 825' includes upper member 826 and lower member 827, which hook onto a face of the bar 810. The bracket 825 allows for the attachment loop assembly to slide, or move, along the length of the arch bar where it is then secured in place by set screw 850.

Optionally, the bar 810 may include a roughened surface 840 to be engaged by the set screw 850, thereby providing traction for the set screw 850 and preventing unintended movement of the attachment loop assembly. The roughened surface 840 also may engage the set screw 850 in such a manner as to prevent or reduce turn-out of the set screw once it is set in place. Such contact may be further enhanced by roughening of the surface of a point of the set screw 850 that engages the roughened surface 140.

In FIG. 7, the attachment loop assemblies 820, 821, 822 are placed between hooks 830, or at the ends of the bar 810. The hooks 830 may be integrally formed with the bar 810 such that they are all formed at the same time and of the same material. In such instances, attachment loop assemblies such as that depicted in FIG. 8B are included to be placed between the hooks 830. Alternatively, the hooks may be threaded on one end, and threaded apertures or depressions, capable of receiving the hooks are included in the bar 810. Such an alternative, the attachment loop assemblies as shown in FIG. 8A may be slid onto the bar before the hooks are engaged to the bar.

As illustrated by the arch bar 800 of FIG. 7, the hooks 830 are spaced so that there is an amount of lateral travel of each attachment loop assembly 820, 821, 822 along the length of the bar 810. This is advantageous in a number of situations including placement of the attachment loop between the roots of teeth, for reduction of fractures of the mandible or maxilla, or to accommodate different features in different patients due to size or other individual needs.

In some embodiments, and as noted above, the bar 810 has one or more additional attachment loop assemblies 822 located between the first 820 and second 821 attachment loop assemblies. For example, the bar 810 may have a third attachment loop assembly 822 located approximately midway between the first 820 and second 821 attachment loop assemblies, thereby providing an additional point of attachment for the bar. Additional attachment loop assemblies may be added as the requirements of the application dictate.

Figure 9:
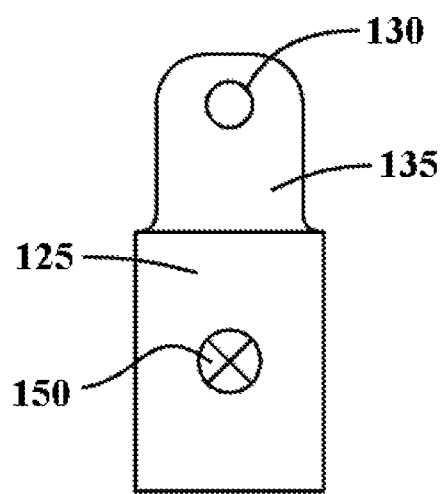
FIG. 9 is a frontal view of a dynamic arch bar loop assembly bracket, according to one embodiment.

The attachment loops 820, 821, 822 provide a point, i.e. attachment loops 830, at which the bar 810 may be secured to a maxilla, a mandible, or a prosthetic appliance using a screw, a bone screw, or other fastener known to those of skill in the art. FIG. 9, is a frontal view of an attachment loop assembly 820, 821, 822 showing the attachment loop 830, stem 835, bracket 825, and set screw 850. In some embodiments, the arch bar 800 includes a third, a fourth, a fifth, a sixth, a seventh, or more attachment loop assemblies spaced along the length of the bar 810.

A variety of fasteners may be used to attach the bar 810 to a maxilla or a mandible. For example, such fasteners may include screws, rivets, bolts, staples, or other fastener known to those of skill in the art. The fasteners are attached to the maxilla or mandible via a variety of systems. For example, a hole for attaching the fastener may be pre-drilled in the maxilla or mandible, or the fastener may be a self-drilling or self-tapping fastener. The size of the fastener may also be varied depending upon the placement desired. For example, mandibles are typically thicker than maxillas and therefore a mandible is capable of receiving a longer and/or wider fastener than the maxilla. Fasteners may also be flush mounted to the gingiva or may have a relief from the gingival surface so that there is some amount of externalization for a surgeon or dental professional to easily find the fastener when removal of the device is desired.

Figure 10:
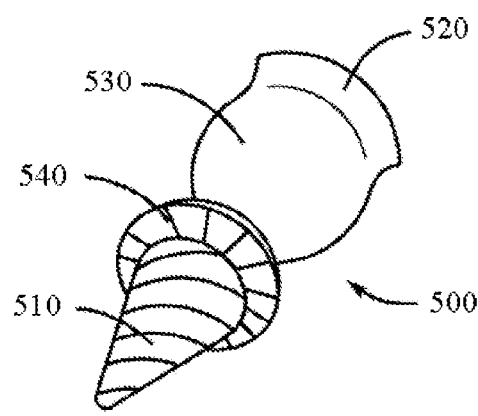
FIG. 10 is a view of a bone screw for attaching the arch bar to a mandible or maxilla, according to one embodiment.

As a non-limiting example of such fasteners, screws 500 may be used to attach the bar 110 to a maxilla or mandible. For example, FIGS. 3 and 10 show views of screws 200, 500, according to various embodiments. Screw 200 is described above. The screw 500 has a head 510 and a thread 520. The screw 500 may have threading that extends to the head 510 to allow for full insertion of the screw 500 into the bone. The screw 500 may alternatively, have a post 530 that would project from the gingiva, or mucosa, when screwed into a mandible or maxilla. Such a post 530 allows the surgeon or other dental professional to readily locate the screw for removal, and as a way to reduce fractures of the mandible or maxilla, as described below. The screw 500 may also have a coarse or serrated underside 540 to the head 510 to aid in "gripping" of the screw to a surface and preventing or reducing undesired turnout of the screw. The drive mechanism for the screw 500 may be of any type known to those of skill in the art. For example the screw 500 may have a slot drive, a Phillips drive, star drive, an Allen drive, or a hex head. The screws may be designed to require tapping (i.e. drilling in the bone or other surface), they may be self-tapping, they may be self-drilling/self-tapping, or other design known to those of skill in the art.

In some embodiments, the base of the head of the screw is of a larger diameter than a shaft of the screw to permit solid coaptation (via surface area contact) of the arch bar flange to the bone, much like a washer. Wire or elastics may then be placed between the hooks of opposing arch bars, precluding the need for a passage hole through the screw, as was common with IMF screw fixation. The screw may project through the gingiva or mucosa for ease in removal, or it may be designed to sit flush with the bone.

To secure the arch bar to the maxilla, the mandible, or the prosthedontic device, insertion of screws into a root should be avoided. In fact, it is desired that the screws are inserted into the bone at a position between the roots of adjacent teeth. Thus, in one aspect of the dynamic arch bar, the attachment loop assemblies are individually positioned between the roots of adjacent teeth to allow for optimal positioning and screw attachment.

As noted above, a plurality of hooks 830 are attached, or formed, to the bar 810. As used herein, plurality may mean one, but typically means more than one, such as two, three, four, five, six, seven, eight, nine, ten, eleven, twelve, thirteen, fourteen, fifteen, sixteen, seventeen, eighteen, nineteen, or twenty. The hooks 830 on the arch bars are used to attach a wire, an elastic such as a rubber band, or other device known to those of skill in the art, to the bar 810 to immobilize, stabilize, or fixate the maxilla to the mandible, thus allowing for healing of the respective bones.

The hooks 830 may be positioned on the arch bar 800 such that the opening is to the attachment loop of the attachment loop assembly. However, in other embodiments, the hook may have the open part of the hook opposed to the attachment loop assembly. The size, shape, and configuration of the hooks may vary according to design preferences. The only limiting feature of the size, shape, and configuration of the hooks 830 is that they must have the ability to satisfactorily allow placement of wire, elastic, or other fasteners to the arch bar 800.

Figure 11:
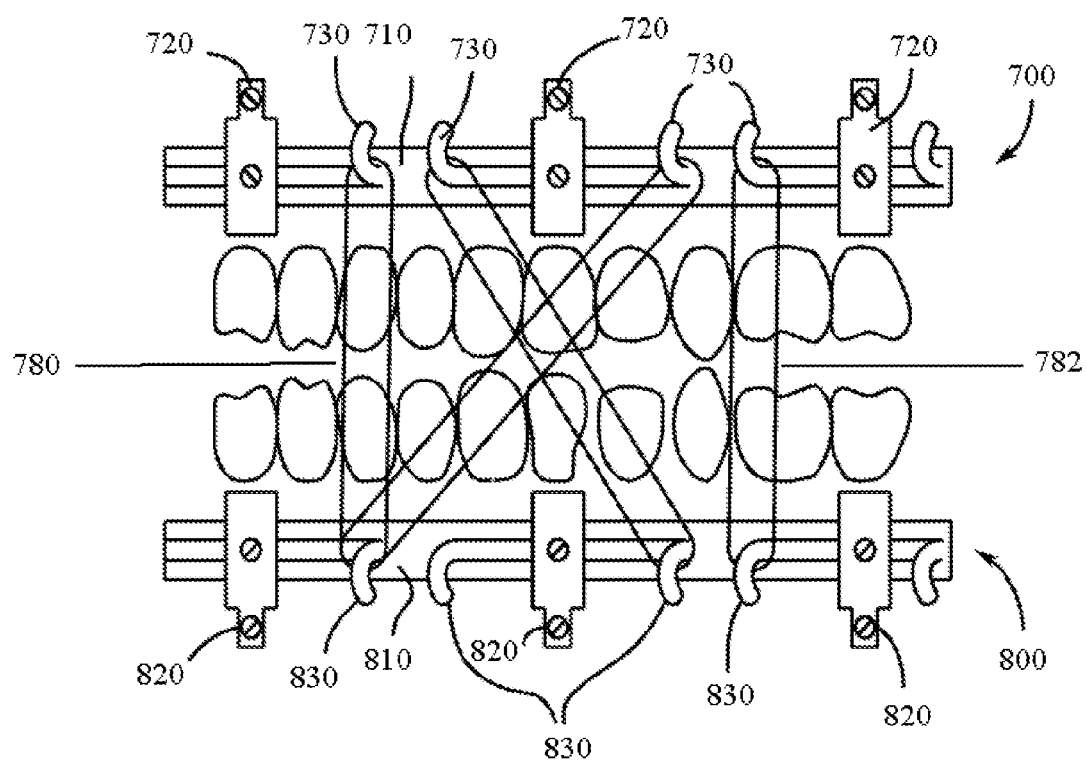
FIG. 11 is a panorex view of a dental arch with two dynamic arch bars connected together via wires, according to one embodiment.

In some aspects, a medical apparatus has two arch bars, as shown in FIG. 11. A first arch bar 900 is attached to the maxilla and a second arch bar 800 is attached to a mandible. The bars 910, 1010 are attached in the same manner as above, i.e. with screws through the two or more attachment loop assemblies 920, 1020. The hooks 930, 1030 on each of the arch bars 900, 1000 opposed to one another so that the securing wires 980, 981, 982, elastics such as rubber bands, or other attachment devices can be hooked to the arch bars 900, 1000 on the maxilla and mandible. The securing wires 980, 981, 982 or other attachment devices may be separate entities as shown in FIG. 11, or a single wire may be intricately woven to attach arch bar 900 to arch bar 800, thus fixating the maxilla and/or mandible.

In another aspect, methods are provided for stabilizing a mandibular arch or a maxillary arch using the medical apparatuses described above. For example, the arch bar may be bent to approximate the mandibular arch or the maxillary arch of a patient in need of stabilization or fixation of the mandibular and/or maxillary arch. Screws are then inserted through the attachment loops, and the screws are then secured into the mandible, maxilla, or a prosthedontic device. In the case where the screws are inserted in the mandible or maxilla, if the attachment loop is not in line with a position that is between the roots of adjacent teeth, the attachment loop assembly may be re-positioned to a desired position and secured in place using the set screws in the assembly.

As described above, the dynamic arch may be used in a method for reducing a fracture of the mandible or maxilla. In the method, an arch bar is set in place along the gingiva of a mandible or maxilla. Screws are inserted, through the attachment loop of an attachment loop assembly into the bone on either side of a fracture. Then, wire or an elastic device may be attached to the posts of the screws to apply tension between the two screws to reduce the fracture. Because the attachment loop assemblies have not been set to the bar with the set screws, the assemblies are free to move along the arch bar as the reduction is made. Once the fracture is reduced the set screws are put in place, and the arch bar is set to maintain the positioning of the reduced fracture. Once set in place, the attachment loop assembly and arch bar keep the fracture reduced for healing. The surgeon, dentist or other medical professional then may decide when the wire or elastic member is removed, either immediately after reduction, or at some time later in the healing process.

In other embodiments, where both a mandibular and a maxillary arch bar are used, the methods also include securing a wire, an elastic, or other flexible or semi-rigid material between the hooks of the mandibular arch bar and the hooks of the maxillary arch bar. This may be done to establish intermaxillary fixation or dental occlusion. Such methods are known as wiring the jaws shut or intermaxillary fixation.

The above described apparatuses and methods are used to restore, fixate, or create anew dental occlusion between existing native dentition, dental implants, or other dental appliances, or for the treatment of fracture and/or reconstructing maxillary and/or mandibular reconstruction.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additionally the phrase "consisting essentially of" will be understood to include those elements specifically recited and those additional elements that do not materially affect the basic and novel characteristics of the claimed invention. The phrase "consisting of" excludes any element not specifically specified.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, it should be understood that changes and modifications can be made therein in accordance with ordinary skill in the art without departing from the invention in its broader aspects as defined in the following claims.

What is claimed is:

1. A medical apparatus comprising:
   a bar having a longitudinal axis;
   a first attachment loop;
   a first screw extending through the first attachment loop and adapted to extend into a mandibular jaw or a maxillary jaw;
   a second attachment loop;
   a second screw extending through the second attachment loop and adapted to extend into the mandibular jaw or maxillary jaw; and
   a plurality of hooks,
   wherein the medical apparatus is an arch bar having a first side extending along the longitudinal axis and a second side extending along the longitudinal axis, the first and second attachment loops being monolithically formed with the bar along the first side and the hooks having an open part that is turned toward the first side, and at least one of the hooks extending between the first attachment loop and the second attachment loop along the longitudinal axis.

2. The medical apparatus of claim 1, wherein the bar comprises a front surface that includes a first plane, and wherein the bar further comprises:
   a first extension that extends from the bar in a direction perpendicular to the first plane, wherein the first extension is fixed to the bar at a first end; and
   a second extension that extends from a second end of the first extension, wherein the second extension extends in a direction parallel to the first plane, and wherein the second extension comprises the first attachment loop.

3. The medical apparatus of claim 1, wherein the bar further comprises:
   a first extension between the first attachment loop and the bar; and
   a second extension between the second attachment loop and the bar.

4. The medical apparatus of claim 3, wherein the first extension and the second extension are bendable.

5. The medical apparatus of claim 4, wherein the first extension and the second extension are bendable in a direction lateral to a length of the bar.

6. The medical apparatus of claim 4, wherein the first extension is bendable to be located adjacent to roots of a first tooth and roots of a second tooth, and wherein the second extension is bendable to be located adjacent to roots of a third tooth and a fourth tooth.

7. A medical apparatus comprising:
   a first attachment loop;
   a first screw extending through the first attachment loop and adapted to extend into a mandibular jaw or a maxillary jaw;
   a second attachment loop;
   a second screw extending through the second attachment loop and adapted to extend into the mandibular jaw or maxillary jaw, the second attachment loop spaced apart from the first attachment loop; and
   a plurality of hooks spaced apart from each other,
   wherein the medical apparatus has a longitudinal axis, first and second sides extending along the longitudinal axis and is bendable to conform to the mandibular jaw or the maxillary jaw, the first and second attachment loops being disposed along the first side and monolithically formed with the medical apparatus, the hooks having an open part that is turned toward the first side, and at least one of the hooks extending between the first attachment loop and the second attachment loop along the longitudinal axis.

8. The medical apparatus of claim 7, further comprising:
   a bar that extends along a portion of a first plane;
   a first extension that extends from the bar in a direction perpendicular to the first plane, wherein the first extension is fixed to the bar at a first end; and
   a second extension that extends from a second end of the first extension, wherein the second extension extends in a direction parallel to the first plane, and wherein the second extension comprises the first attachment loop.

9. The medical apparatus of claim 8, wherein the plurality of hooks are fixed to the bar.

10. A medical apparatus comprising:
    a first attachment loop;
    a first screw extending through the first attachment loop and adapted to extend into a mandibular jaw or a maxillary jaw;
    a second attachment loop spaced apart and connected to the first attachment loop;
    a second screw extending through the second attachment loop and adapted to extend into the mandibular jaw or maxillary jaw; and
    a plurality of hooks,
    wherein the medical apparatus has a longitudinal axis and a first side and a second side extending along the longitudinal axis, the first and second attachment loops being disposed along the first side and monolithically formed with the medical apparatus, and the hooks having an open part that is turned toward the first side, and at least one of the hooks extending between the first attachment loop and the second attachment loop along the longitudinal axis.

11. The medical apparatus of claim 10, wherein the first and second attachment loops are connected by a bar.

12. The medical apparatus of claim 11, wherein the plurality of hooks are attached to the bar.

13. The medical apparatus of claim 11, wherein the first attachment loop is attached to the bar by a first extension and the second attachment loop is attached to the bar by a second extension.

14. The medical apparatus of claim 13, wherein the first extension and the second extension are bendable.

15. The medical apparatus of claim 10, further comprising a third attachment loop.

* * * * *